US00PP24836P3

(12) United States Plant Patent
Slaughter et al.

(10) Patent No.: US PP24,836 P3
(45) Date of Patent: Sep. 2, 2014

(54) PEACH TREE, 'BURPEACHTHIRTY'

(50) Latin Name: *Prunus persica*
Varietal Denomination: Burpeachthirty

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 77 days.

(21) Appl. No.: 13/694,648

(22) Filed: Dec. 20, 2012

(65) Prior Publication Data

US 2014/0182023 P1 Jun. 26, 2014

(51) Int. Cl.
*A01H 5/00* (2006.01)

(52) U.S. Cl.
USPC ..... Plt./197

(58) Field of Classification Search
USPC ..... Plt./197
See application file for complete search history.

*Primary Examiner* — Annette Para
(74) *Attorney, Agent, or Firm* — Paine Hamblen, LLP

(57) ABSTRACT

A new and distinct variety of peach tree (*Prunus persica*), which is denominated varietally as 'Burpeachthirty', and which produces an attractively colored yellow-white fleshed, clingstone peach which is mature for harvesting and shipment approximately October 7 to October 17 under the ecological conditions prevailing in the San Joaquin Valley of central California.

1 Drawing Sheet

Botanical designation: The present invention relates to a new, novel, and distinct variety of peach tree, '*Prunus persica*'.

Varietal denomination: 'Burpeachthirty'.

BACKGROUND OF THE NEW VARIETY

The present variety of peach tree resulted from an on-going program of fruit and nut tree breeding. The purpose of this program is to improve the commercial quality of deciduous fruit and nut varieties, and rootstocks, by creating and releasing promising selections of *prunus, malus* and *juglans* species. To this end we make both controlled and hybrid cross pollinations each year in order to produce seedling populations from which improved progenies are evaluated and selected.

The seedling, 'Burpeachthirty' was originated by us, and selected from a population of seedlings growing in our experimental orchards which are located near Fowler, Calif. The seedlings, grown on their own roots, were derived from a cross using the 'Fayette' peach tree (unpatented, released by USDA ARS Fresno, Calif. in 1937), and which was used as the seed parent; and an unnamed yellow-fleshed clingstone peach which was used as the pollen parent. After a period of stratification, the seed was placed in the greenhouse by population, and then field planted for tree establishment, and ultimately to exhibit fruit for evaluation. One yellow fleshed peach seedling, which is the present variety, exhibited especially desirable characteristics, and was then designated as 'C9.053'. This seedling was marked for subsequent observation. After the 1999 fruiting season, the new variety of peach tree was selected for advanced evaluation and repropagation.

ASEXUAL REPRODUCTION

Asexual reproduction of this new and distinct variety of peach tree was accomplished by budding the new peach tree onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachthirty' is a new and distinct variety of peach tree, which is considered of medium-large size, and which has a moderately vigorous growth characteristic. This new tree is also a regular and productive bearer of relatively large, firm, yellow-fleshed, clingstone fruit which have a very good flavor, and eating qualities. This new peach tree has a medium chilling requirement of approximately 650 hours, and further produces relatively uniformly sized fruit throughout the tree's canopy. In addition to the foregoing, the fruit of the new peach also appears to have good handling and shipping qualities. The 'Burpeachthirty' peach tree bears fruit which are typically ripe for commercial harvesting and shipment on approximately October 7 to October 17 under the ecological conditions prevailing in the San Joaquin Valley of central California. In relative comparison to the 'Burpeacheighteen' peach tree (U.S. Plant Pat. No. 15,496), which is the closest known variety, the new variety of peach tree bears fruit that ripens approximately 2 weeks later. In relative comparison to the pollen parent, 'Fayette' peach tree, the present variety ripens approximately 3 weeks later.

BRIEF DESCRIPTION OF THE DRAWINGS

The accompanying drawing, which is provided, is a color photograph of the new peach tree variety.

The photograph depicts two whole mature fruit showing the top and bottom characteristics thereof, and one mature fruit bisected transversely below the equatorial plane, and which reveals the flesh color, and stone characteristics thereof. The external coloration of the fruit as shown in the photograph is sufficiently matured for harvesting and shipment. Additionally, the photograph displays a sample vegetative shoot bearing typical leaves, and a typical stone with the flesh removed. The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the seventh fruiting season, and under the ecological conditions prevailing at the orchards of the assignee which are located near the town of Fowler, county of Fresno, state of California. All major color code designations are by reference to The R.H.S. Colour Chart (Fourth Edition, 2001) provided by The Royal Horticultural Society of Great Britain. Common color names are also occasionally used.

TREE

Size: Generally considered medium to medium-large in its growth pattern as compared to other common commercial peach cultivars ripening in the late season of maturity. The tree of the present variety was pruned to a height of approximately 270.0 cm. to about 310.0 cm. at commercial maturity.

Width: Approximately 280.0 cm.

Vigor: Considered moderately vigorous. The present peach tree variety grew from about 168.0 cm. to about 170.0 cm. in height during the first growing season. The new variety was pruned to a height of approximately 150.0 cm. during the first dormant season, and primary scaffolds were then selected for the desired tree structure.

Productivity: Productive. Fruit set varies from more than the desired crop load, to levels higher than desired levels, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

Fruit bearing: Regular. Fruit set has been more than adequate during the previous years of observation, and thinning was necessary during the past 10 years on both the original seedling and on subsequent asexually reproduced trees.

Tree form: Upright, and pruned into a vase shape.

Density: Considered moderately dense. It has been discovered that pruning the branches from the center of the tree to obtain a resulting vase shape allows for enhanced air movement and appropriate amounts of sunlight to improve fruit color, and renewal of fruiting wood throughout the tree.

Hardiness: The present tree was grown and evaluated in USDA Hardiness Zone 9. The calculated winter chilling requirements of the new tree is approximately 650 hours at a temperature below 7.0 degrees C. The present variety appears to be hardy under typical central San Joaquin Valley climatic conditions.

TRUNK

Diameter: Approximately 18.5 cm in diameter when measured at a distance of approximately 15.24 cm. above the soil level. This measurement was taken at the end of the tenth growing season.

Bark texture: Considered moderately rough, with numerous folds of papery scarfskin being present. Since bark development and coloration change with advancing tree age this characteristic varies with the tree vigor, age and regional conditions. Therefore, this is not a dependable descriptor of the new variety.

Lenticels: Numerous flat, oval lenticels are present. The lenticels range in size from approximately 3.0 millimeters to about 5.0 mm. in width, and between about 1.0 and about 2.0 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark) and therefore become less apparent.

Lenticel color: Considered an orange brown, (RHS Greyed-Orange Group N167 B).

Bark coloration: Variable, but it is generally considered to be a greyed brown, (RHS Greyed-Brown Group N200 A). This bark description was taken from trees in their seventh leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

Size: Considered medium for the variety.

Diameter: Average as compared to other peach varieties. The branches have a diameter of about 11.0 centimeters when measured during the tenth year after grafting.

Surface texture: Average, and appearing furrowed on wood which is several years old.

Crotch angles: Primary branches are considered variable, and are usually growing at an angle of about 45 to about 57 degrees when measured from a horizontal plane. This characteristic can be influenced, to some degree, by tree vigor, rootstock and other cultural conditions.

Current season shoots: Surface texture—Substantially glabrous.

Internode length: Approximately 2.1 cm.

Color of mature branches: Grey brown, (RHS Brown Group N200 A).

Current seasons shoots:

*Color*.—Medium-light green, (RHS Yellow-Green Group 143 B). The color of new shoot tips is considered a bright and shiny green (RHS Green Group 144 B). The vegetative shoot color can be significantly influenced by plant nutrition, irrigation practices, and exposure to sunlight, and therefore should not be considered a consistent botanical characteristic of this new variety.

LEAVES

Size: Considered medium-large for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and other cultural factors listed above, and are not typically considered a dependable botanical descriptor.

Leaf length: Approximately 155.0 to about 175.0 millimeters.

Leaf width: Approximately 31.0 to about 39.0 millimeters.

Leaf base-shape: The leaves generally exhibit equal marginal symmetry relative to the leaf longitudinal axis.

Leaf form: Lanceolate.

Leaf tip form: Acuminate.

Leaf color: Upper Leaf Surface—Dark green, (approximately RHS Green Group 135 A).

Leaf texture: Glabrous.

Leaf color: Lower Leaf Surface—light to medium green, (approximately RHS Green Group 139 B).

Leaf venation: Pinnately veined.

Mid-vein:

*Color*.—Considered a light, yellow-green, (approximately RHS Yellow-Green Group N144 C) in the early to mid-period of the growing season.

Leaf margins: Gently undulating.

*Form*.—Considered crenate.

*Uniformity*.—Considered generally uniform.

Leaf petioles:

*Form*.—Considered canaliculated, and having a more pronounced trough when viewed from the dorsal aspect. The petiole margin is considered rounded when viewed from the ventral aspect.

*Size*.—Considered medium-small for the species.

*Length*.—About 7.0 to about 11.0 mm.

*Diameter*.—About 1.5 to about 2.5 mm.

*Color*.—Light yellow green, (approximately RHS Yellow-Green Group 144 B).

Leaf glands:

*Size*.—Considered small for the species; approximately 1.0 mm. in length; and about 1.0 mm. in height.

*Number*.—Generally one to two glands per marginal side are found. Observations of more than two glands per marginal side are more uncommon.

*Type*.—Glands located at the base of the leaf are predominantly reniform in shape. An additional one to two, or occasionally more glands, which appear more globose, and stalked, are often present at the basal margin of the leaf petiole as well.

*Color*.—Considered a medium, light brown, approximately (RHS Grey-Brown Group 199 B). Typically the coloration of the glands darkens, and occasionally begins to desiccate during, and thereafter, the mid-late growing season.

Leaf stipules:

*Size*.—Medium large for this variety.

*Number*.—Typically 2 per leaf bud, and up to 6 per shoot tip.

*Form*.—Lanceolate in form, and having a serrated marginal edge.

*Color*.—Green, (approximately RHS Green Group 139 B) when young, but graduating to a brown color, (approximately RHS Greyed-Orange Group 165 A) with advancing senescence. The leaf stipules are generally considered to be early deciduous.

FLOWER BUDS

Hardiness: No winter injury (bud death) has been noted during the last several years of observation in the central San Joaquin Valley. The new variety of peach tree has not been intentionally subjected to drought, cold or heat stress, and therefore this information is not available.

Flower bud:

*Size*.—Variable, and dependent on the state of maturity. The flower buds as described were observed approximately 7 days prior to bloom.

Flower bud:

*Length*.—Approximately 13.0 millimeters.

Flower bud:

*Diameter*.—Approximately 9.5 millimeters.

Flower bud surface texture: Pubescent.

Flower bud orientation: Considered appressed, but appear less so as the blossoms near opening.

Bud scale color: Approximately RHS Greyed-Purple 187 A.

FLOWERS

Date of first bloom: Observed on Feb. 26, 2012.

Blooming time: Considered average in relative comparison to other commercial peach cultivars grown in the central San Joaquin Valley. The date of full bloom was observed on Mar. 5, 2012. The date of full bloom varies slightly with climatic conditions, and prevailing cultural practices.

Duration of bloom: Approximately 7 days. This particular characteristic varies slightly with the prevailing climatic conditions.

Flower class: Considered a perfect flower, complete and perigynous.

Flower type: The variety is considered to have a showy type flower.

Flower size: Considered medium. The flower diameter at full bloom, is approximately 29.0 to 32.0 millimeters.

Bloom quantity: Considered abundant.

Flower bud frequency: Normally two flower buds appear per node, occasionally one flower bud per node is observed.

Petal size: Generally considered medium for the species.

*Petal length*.—Approximately 13.0 to 18.0 millimeters.

*Petal width*.—Approximately 12.0 to 15.0 millimeters.

Petal form: Considered broadly ovate.

Petal count: Nearly always 5.

Petal texture: Glabrous.

Petal color: Considered a light pink at the popcorn stage, (RHS Red Group 49 B), and darkening with advanced senescence, and the exposure of sunlight, to a medium-dark pink, (RHS Red-Purple 64 D).

Fragrance: Slight.

Petal claw:

*Form*.—The claw is considered truncate, and is generally medium-small when compared to other varieties.

*Length*.—Approximately 7.0-8.0 millimeters.

*Width*.—Approximately 6.0 to 8.0 millimeters.

Petal margins: Generally considered variable, from nearly smooth to moderately undulate and ruffled, especially apically.

Petal apex: Generally, the petal margin is entire at tip.

Flower pedicel:

*Length*.—Considered medium-long with an approximate length of about 0.5 to about 1.0 millimeters.

*Diameter*.—Approximately 1.0 millimeters.

*Color*.—A medium brown, approximately (RHS Grey-Brown Group N199 D).

*Surface*.—Glabrous.

Floral nectaries:

*Color*.—Considered a deep orange (approximately RHS Greyed-Orange Group N172 B).

Calyx:

*Surface texture*.—Generally glabrous.

*Color*.—A dull red, (approximately RHS Greyed-Purple Group 183 A).

Sepals:

*Surface texture*.—The surface has a short, fine pubescent texture.

*Number*.—5 sepals.

*Size*.—Average, and ovate in form.

*Sepal length*.—Approximately 4.0 to 6.0 millimeters.

*Sepal width*.—Approximately 4.0 to 6.0 millimeters.

*Sepal shape*.—Generally obovate.

*Sepal margin*.—Considered smooth and entire.

*Sepal color*.—A dull, magenta, (approximately RHS Greyed-Red Group 181 C).

Anthers:

*Generally*.—Average in size.

*Color*.—Red to reddish-orange when viewed dorsally and prior to dehiscence, (approximately RHS Greyed-Red Group 179 A).

Pollen production: Pollen is abundant and has a yellow color, (approximately RHS Yellow-Orange Group 17 B).

Fertility: Self-fertile.

Filaments:

*Size*.—Approximately 13.0 to 16.0 millimeters in length.

*Color*.—Considered white to a pinkish-white, (RHS Red Purple Group 62 D).

Pistil:

*Number*.—Usually one, and only rarely more than one.

*Generally*.—Large in size.

*Length*.—Approximately 17.0 to about 19.5 millimeters in length including the ovary.

*Color*.—Considered a very pale green, (approximately RHS Yellow-Green Group 150 D).

*Surface texture*.—The variety has a long pubescent pistil.

FRUIT

Maturity when described: Firm ripe condition (shipping ripe).

Date of first picking: Approximately Oct. 7, 2012 Date of last picking—Oct. 17, 2012. The date of harvest can vary slightly with the prevailing climatic conditions and the current cultural practices.

Size: Generally—Considered large, and uniform.

Average cheek diameter: Approximately 70.0 to about 92.0 millimeters.

Average axial diameter: Approximately 68.0 to about 87.0 millimeters.

Typical weight: Approximately 235.0 grams. This characteristic is quite dependent upon the prevailing cultural practices, and therefore is not particularly distinctive of the new variety.

Fruit form:

*Generally*.—Considered globose. The fruit is generally uniform in symmetry.

Fruit suture: Some slight stitching exists along the suture line.

Suture:

*Color*.—Generally, the fruit appears blushed to the same degree as the skin, (approximately RHS Red Group 46 B).

Ventral surface:

*Form*.—Quite even, and uniform in appearance, when it is viewed from the lateral, sutural plane.

Apex:

*Shape*.—Rounded to slightly retuse.

Base:

*Shape*.—Generally smooth.

Stem cavity:

*Generally*.—It extends in a rounded circular form which is generally considered uniform. The stem cavity is rounded but slightly extended toward the suture. The average depth of the stem cavity is about 8.0-10.0 mm. The average width of the stem cavity is about 30.0 mm. The average length of the stem cavity, when measured in the suturial plane. is about 55.0 mm.

Fruit skin:

*Thickness*.—Considered medium in thickness, and tenacious to the flesh.

*Surface texture*.—Short, fine and pubescent. The pubescence is moderately abundant.

*Taste*.—Non-astringent.

*Tendency to crack*.—Not observed in the previous years of observation and evaluation.

Fruit skin color:

*Blush color*.—Generally speaking, a red blush exists on a majority of the skin of the fruit (approximately RHS Red Group 46 B), and is more typically present on the portions of the fruit facing the sunlight. The blush of the fruit typically covers approximately 35%-45% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown.

Ground color: Yellow, (approximately RHS Yellow Group 13 C). The ground color of the fruit can vary significantly based upon the maturity of the fruit when this measurement is taken.

Fruit stem:

*Size*.—Medium in length, approximately 6.0 to about 8.0 millimeters.

*Diameter*.—Approximately 2.0 to about 3.0 millimeters.

*Color*.—Pale yellow-green, (approximately RHS Yellow-Green Group N144 C).

Fruit flesh:

*Ripening*.—Considered even.

*Texture*.—Firm, juicy and dense. Considered firm yet non-melting.

*Fibers*.—Present but not prominent.

*Aroma*.—Slight.

*Eating quality*.—Considered very good.

*Flavor*.—Considered very sweet, and with moderate acidity. The flavor is considered both pleasant and balanced.

*Juice production*.—Moderate.

*Brix*.—About 14.50 to 17.0 degrees. This characteristic varies slightly with the number of fruit per tree; the maturity of fruit when harvested; the prevailing cultural practices; and the ambient climatic conditions.

*Flesh color*.—It is considered a yellowed white, (approximately RHS Yellow Group 11 A).

STONE

Type: Considered a clingstone.

Size: It is generally considered to be medium-small for the variety. The stone size varies significantly depending upon the tree vigor, the crop load, and the prevailing growing and cultural conditions under which the tree was grown.

Length: Average, about 29.0 to about 31.0 millimeters.

Width: Average, about 22.0 to about 26.0 millimeters.

Diameter: Average, about 18.0 to about 20.0 millimeters.

Form: Roughly ovoid.

Stone base: Shape—The stone is considered shortly attenuate.

Apex: Shape—The stone exhibits a slight to prominently acute apex.

Stone surface:

*Surface texture*.—Considered irregularly furrowed toward the apex. Further, more pitting exists in the mid-portion of the stone (laterally), and is more common toward the base.

*Ridges*.—Ridging is generally more prominent, and is usually oriented parallel, and laterally relative at the ventral and dorsal margins.

*Ventral edge*.—The ventral edge is generally considered troughed with three substantial grooves that converge apically.

*Dorsal edge*.—Shape — Generally considered even. The folds of the surface ridges appearing on the external margins often end gently along the suture.

Stone color: The color of a mature, dry stone is generally considered a dull brown, approximately (RHS Greyed-Orange Group 177 A).

Tendency to split: Splitting has rarely been noted.

Kernel:

*Length*.—Approximately 19.0-21.0 millimeters.

*Width*.—Approximately 13.0-15.0 millimeters.

*Thickness*.—5.0-6.0 millimeters.

*Size*.—The kernel is considered medium in size. Further the kernel is gelatinous and immature when the fruit is fully mature, and ready for harvesting and shipment.

*Form*.—Considered generally ovoid.

*Pellicle*.—Slightly pubescent.

*Color*.—A dark tan (RHS Greyed-Orange Group 165 B).

Use: The present variety 'Burpeachthirty' is considered to be a peach tree of the late season of maturity, and which produces fruit which are considered to be firm, attractively colored, and which are useful for both local and long distance shipping.

Keeping quality: Appears excellent. The fruit of the present variety has stored well for periods of up to 30 days after harvest at 1.0 degree Celsius.

Shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been intentionally tested to expose or detect any susceptibilities or resistances to any known plant, fruit diseases, insect, frost, winter injury or other environmental factors.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by Plant Letters Patent is:

1. A new distinct variety of peach tree, substantially as illustrated and described, and which is characterized principally as to novelty by producing an attractively colored yellow-white fleshed, clingstone peach which is mature for harvesting and shipment approximately October 7 to October 17 under the ecological conditions prevailing in the San Joaquin Valley of central California.

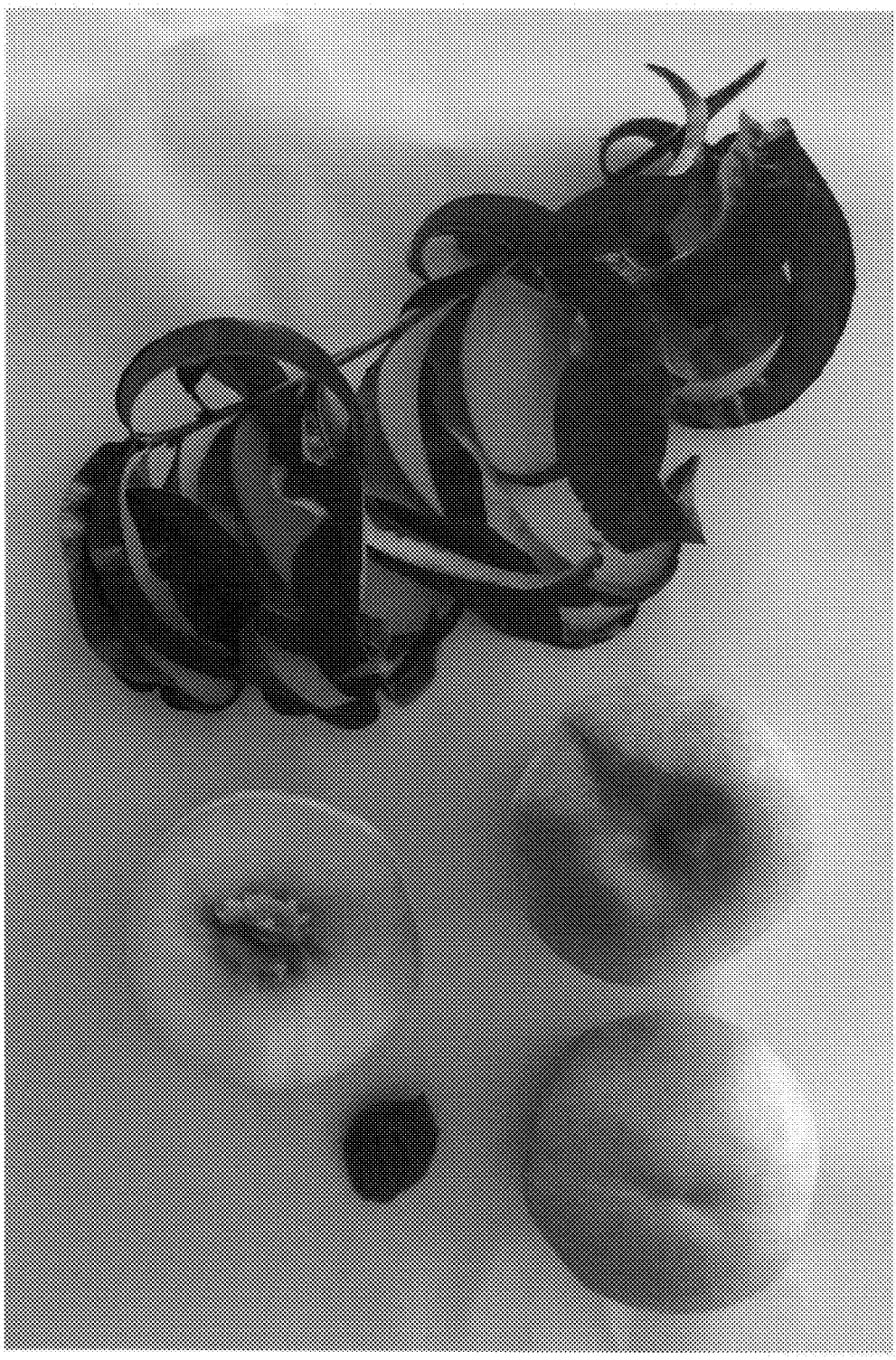

* * * * *